(12) United States Patent
Thomas-Benedict

(10) Patent No.: US 6,974,224 B2
(45) Date of Patent: Dec. 13, 2005

(54) MODULARIZED LIGHT PROCESSING OF BODY COMPONENTS

(75) Inventor: Mellen Thomas-Benedict, Aptos, CA (US)

(73) Assignee: Tru-Light Corporation, Aptos, CA (US)

( * ) Notice: Subject to any disclaimer, the term of this patent is extended or adjusted under 35 U.S.C. 154(b) by 69 days.

(21) Appl. No.: 10/632,542

(22) Filed: Jul. 30, 2003

(65) Prior Publication Data

US 2005/0024853 A1 Feb. 3, 2005

(51) Int. Cl.$^7$ .............................................. F21V 21/08
(52) U.S. Cl. ..................... 362/103; 362/231; 607/88; 128/898
(58) Field of Search ........................ 362/231, 235, 362/804, 800, 103; 607/88–91; 128/898, 828; 606/3, 9, 13

(56) References Cited

U.S. PATENT DOCUMENTS

| | | | | |
|---|---|---|---|---|
| 4,930,504 | A | | 6/1990 | Diamantopoulos et al. . 128/395 |
| 5,312,396 | A | * | 5/1994 | Feld et al. ..................... 606/11 |
| 5,766,233 | A | | 6/1998 | Triberg ........................ 607/88 |
| 5,800,479 | A | * | 9/1998 | Thiberg ........................ 607/88 |
| 6,063,108 | A | * | 5/2000 | Salansky et al. .............. 607/89 |
| 6,238,424 | B1 | * | 5/2001 | Thiberg ........................ 607/88 |
| 6,443,978 | B1 | | 9/2002 | Zharov ........................ 607/91 |
| 6,454,789 | B1 | | 9/2002 | Chen et al. .................... 607/88 |
| 6,482,199 | B1 | | 11/2002 | Neev ............................ 606/10 |
| 6,524,329 | B1 | * | 2/2003 | Benedict ....................... 607/88 |

OTHER PUBLICATIONS

Text and drawings of application of U.S. Appl. No. 10/159,463.
Text and drawings of application of U.S. Appl. No. 10/370,330.
Textbook excerpt available at: www.amazon.com/gp/reader/9056991086/ref=sib_dp_pt/102–0788981–0683330#reader–link, "The Science of Low–Power Laser Therapy", Gordon and Breach, 1998.
Website printout: "Electro–Physiology, Light, and Facial Rejuvenation", 5 pages.
Raum und Zeit, "Meridians Conduct Light", vol. 35, (88), 1991, pp. 16–18.
T. Karu, "Photobiology of Low–Power Laser Effects", Health Physics, vol. 56, No. 5, May 1989, pp. 691–705.

* cited by examiner

*Primary Examiner*—Ali Alavi
(74) *Attorney, Agent, or Firm*—Schneck & Schneck; Thomas Schneck

(57) ABSTRACT

Method and system for illuminating a selected body component with light to encourage selected beneficial reactions of the body component as a result of such exposure and to provide phototherapy. Light is provided using a light delivery module having one or more components that fit around a body component (e.g., as an electronic bandaid), or fit within a mouth or other body cavity, for dental or mouth interior or cavity interior therapy, or are located at a particular site (such as an acupuncture terminal) on the body, where each light delivery component can be independently controlled and can be supplemented by one or more magnetic fields. The body component is exposed to light in first and second substantially nonoverlapping wavelength ranges and to light in third and fourth substantially nonoverlapping wavelength ranges, in a first time interval and in a second time interval, respectively, that are separated by a selected dark field time interval where substantially no light exposure occurs, except for ambient lighting. An integrated power supply allows operation and recharging simultaneously and/or provides power for two or more related light delivery elements at related times. Phototherapy can be provided as a replacement for, or supplement to, conventional acupuncture treatment.

52 Claims, 13 Drawing Sheets

Fig._2

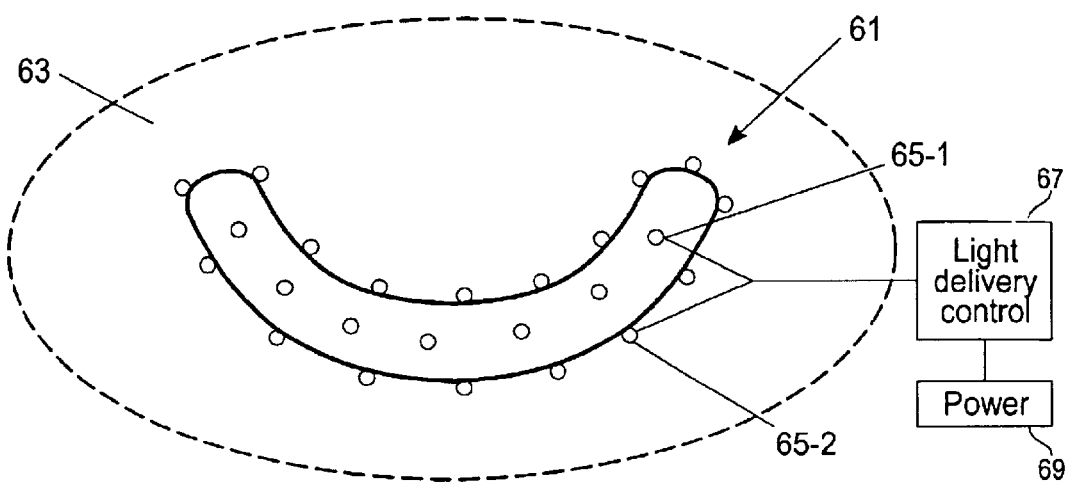
Fig._5
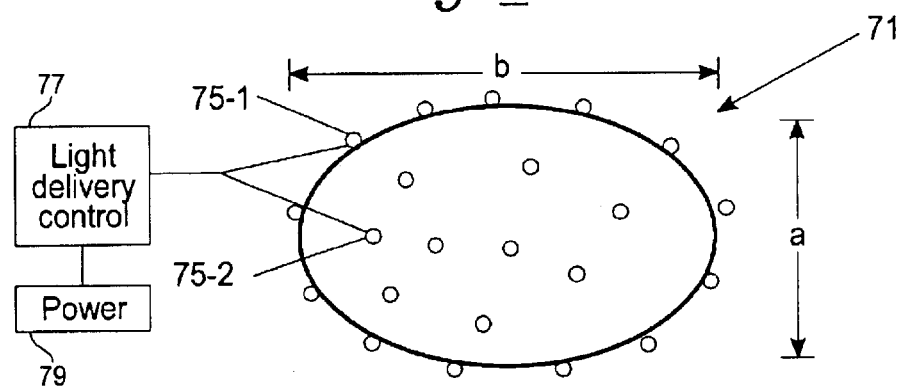
Fig._6
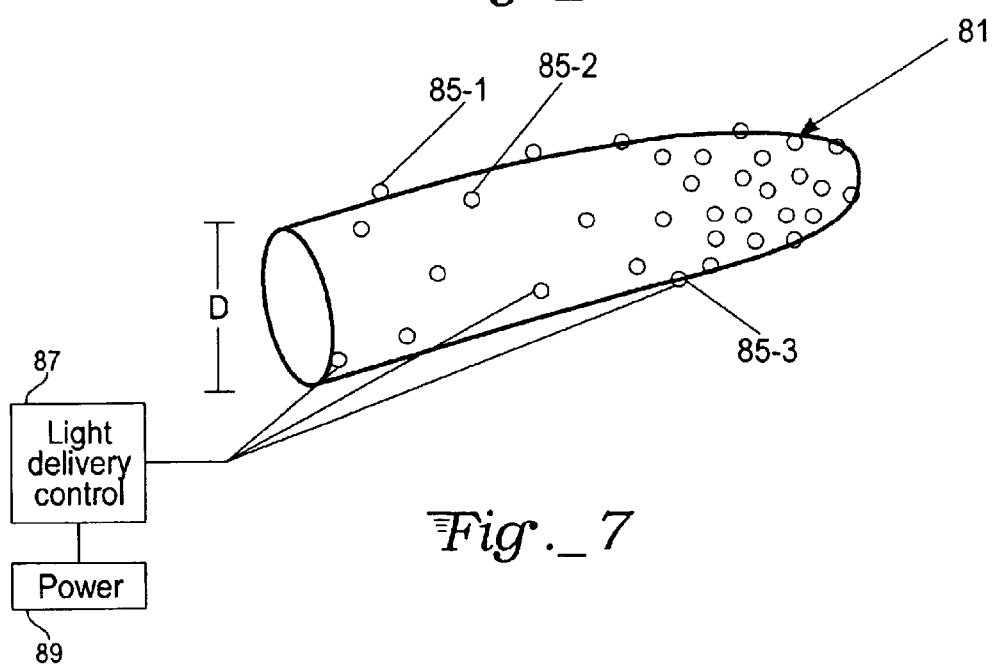
Fig._7

… …

MODULARIZED LIGHT PROCESSING OF BODY COMPONENTS

FIELD OF THE INVENTION

This invention relates to illumination of a selected body component, or a few adjacent components, using light with selected wavelength ranges and selected illumination time intervals.

BACKGROUND OF THE INVENTION

Phototherapy involves generation of light by suitable light sources, such as light emitting diodes (LEDs) in the visible and infrared ranges to provide various benefits for a patient's body. The photons produced are absorbed by the body through the skin, the eyes and acupuncture points or meridians. Connective tissues in the body conduct the light to deeper tissues and organs. By taking advantage of optical properties of biological tissues, suitable wavelengths of light can be delivered to, absorbed by and used by the body to activate metabolic functions.

Treatment of a body using light irradiation requires a choice of several important parameters, including wavelength range, relative distribution of the wavelengths within the range (spectrum), time interval for continuous exposure, time interval between two continuous exposures, time rate of energy delivered, accumulated energy density for exposures, body component(s) irradiated, and many others.

What is needed is a method and corresponding system that provides appropriate illumination for a body component and appropriate choice of the relevant parameters and that distinguishes between treatments for different medical purposes. Preferably, the method and system should provide for, and distinguish between, initial treatments and maintenance treatments for a given medical condition and should cover a large number of, if not all of, conditions that are believed to be treatable using illumination.

SUMMARY OF THE INVENTION

These needs are met by the invention, which provides application of radiation in selected wavelength ranges to a whole body, to a selected body component, or to a few adjacent body components, using a controlled sequence of exposures that illuminate the targeted body components. Any two consecutive time intervals of continuous radiation exposure are spaced apart by a "dark field" time interval whose length is at least equal to a threshold value, in order to re-establish a randomization of electron transport and distribution resulting from application of photons during a continuous exposure interval. Radiation is delivered to one or more selected (adjacent) body components, using an enhanced focussing system that increases the efficiency of delivery of the radiation. The radiation delivery system can be fitted or molded to preferentially illuminate only the desired body components. Several different modules are provided, including light delivery components that can be combined or used in stand-alone mode for delivery of light to part or all of the head, the interior of the mouth, one or more selected body parts and/or one or more selected acupuncture sites. Light therapy in or near the visible range can be combined with static or time-varying magnetic fields to provide additional effects and benefits.

BRIEF DESCRIPTION OF THE DRAWINGS

FIGS. 1–12 schematically illustrate apparatus for delivery of radiation to selected (adjacent) body components according to embodiments of the invention.

DESCRIPTION OF BEST MODES OF THE INVENTION

Figure 1:
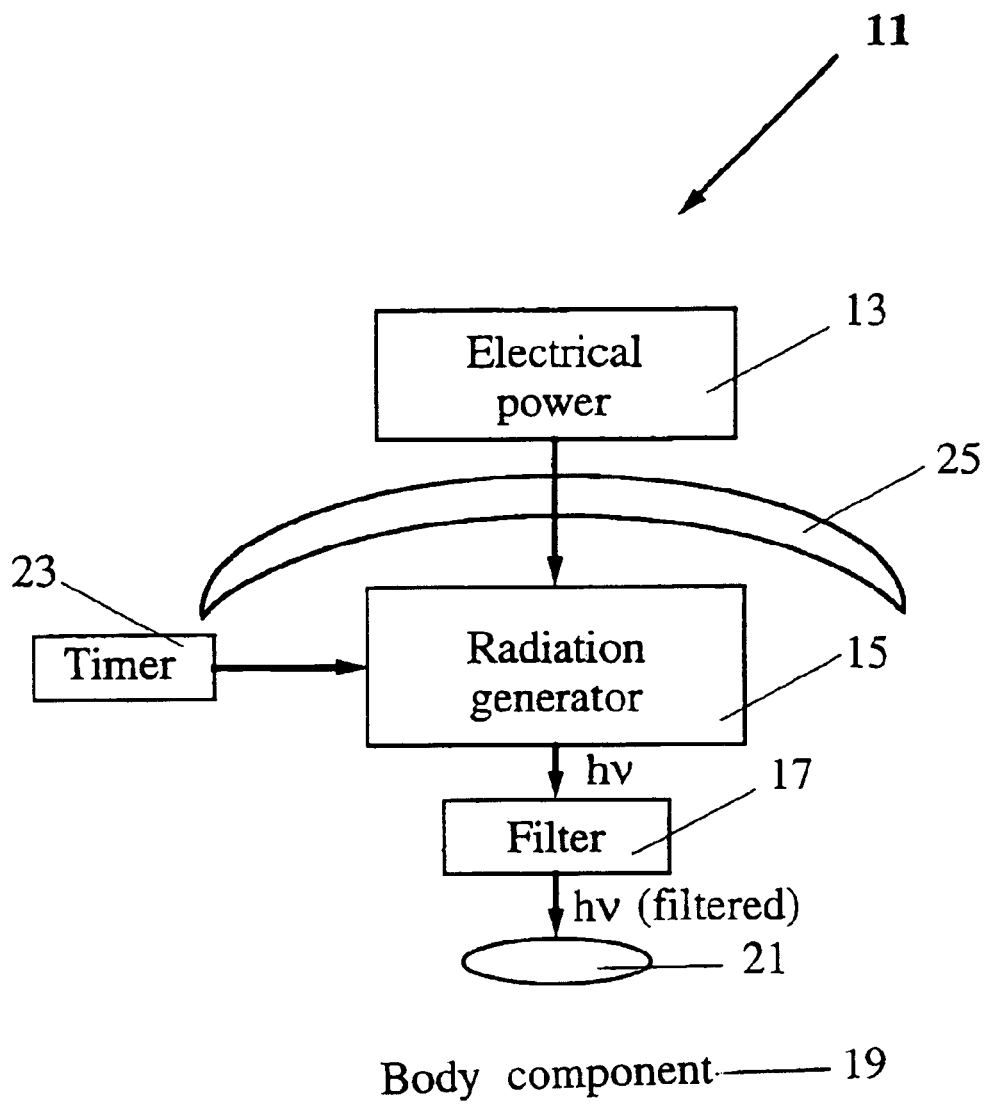

FIG. 1 illustrates a light delivery wrap system 11 suitable for generating and delivering radiation to one or more selected body components according to the invention. The system 11 includes an electrical power source 13 that delivers controllable power to an assembly 15 of generators of electromagnetic radiation in the form of light in the visible and near infrared ranges (e.g., with wavelengths $\lambda$ in a range 400 nm $\leq \lambda \leq$ 1500 nm). Optionally, the light generated by the radiation generator assembly 15 also may have wavelengths in a near-ultraviolet range (e.g., 350 nm $\leq \lambda \leq$ 400 nm) and may have longer wavelengths in a mid-infrared range ($\lambda$>1500 nm), or in selected portions of one or more of these wavelength ranges.

Each radiation generator in the assembly 15 may be a laser, a light emitting diode, an intense incandescent light source, an intense fluorescent light source or any other suitable intense light source, or a combination of two or more such light sources. Preferably, the radiation generator assembly 15 is positioned on a light delivery wrap mechanism 16 that is configured to contact and wrap around a selected body component 19, a group of two or more adjacent body components or the whole body, so that each radiation generator is spaced apart from the body component 19 by at least a selected threshold distance d(thr), to provide some control over the rate at which light is delivered to this body component. A suitable threshold distance is d(thr)= 1–10 cm. However, direct contact with the body is appropriate in some instances. If the assembly 15 provides light in one or more unwanted wavelength ranges, one or more filters 17 (optional) may be positioned between the radiation generator assembly 15 and the selected body component(s) 19 to be treated. The radiation generator assembly 15 may produce a single or a few beams of light that are directed toward the body component 19, considered as a target. Preferably, the radiation generator assembly 15 produces many light beams that are directed toward the body component 19. The system optionally includes a light focussing mechanism 21 that preferentially directs light produced by the radiation generator assembly 15 toward one or more target sites 19-j (j=1, 2, . . . ). In some situations, the light beams are produced in a pattern surrounding a selected body part, such as an arm or a leg, so that the selected body part and adjacent body parts are irradiated together in a (diffuse) field effect.

The radiation generator assembly 15 includes a timer 23 that activates and deactivates (turns on and turns off) the radiation generator during selected exposure time intervals, with any two consecutive continuous exposure (light) time intervals having a first selected length $\Delta t(exp)$, separated by a dark field time interval that has a second selected length Δt(dark). This (light/dark/light) activity and its inverse (dark/light/dark) are sometimes referred to as a "reciprocating chase." The first selected length lies in a preferred range 0.1 sec≦Δt(exp)≦1 sec, and the second selected length Δt(dark) is preferably between 0.1 sec and 1 sec.

A light reflecting mechanism 25 (optional) is positioned adjacent to the radiation generator assembly 15 to capture and direct light toward the selected body component 19 to couple some or all of the generated light that would otherwise have been lost into that body component. A light concentrator, condenser or other light focussing mechanism 21 (optional) is positioned between the radiation generator assembly 15 and the body component 19, to selectably concentrate (or to scatter within the body) the generated light on and around the body component 19, the whole body or selected sites on the selected body component.

In FIG. 1, the selected body component 19 is a portion of, or all of, the head. The radiation generator assembly 15 optionally includes a first assembly component 15A that wraps around the chin, mouth and jaws of a patient, and optionally provides radiation within the patient's mouth, and a second assembly component 15B that wraps around the upper jaws, nose, eyes, ears, forehead, upper neck and uppermost portion of the head of the patient. Optionally, the first and second assembly components, 15A and 15B, can be hooked together to form a unitary assembly 15 and can be disassembled into two or more components, such as 15A and 15B, to illuminate separate groups of body components.

Figure 2:
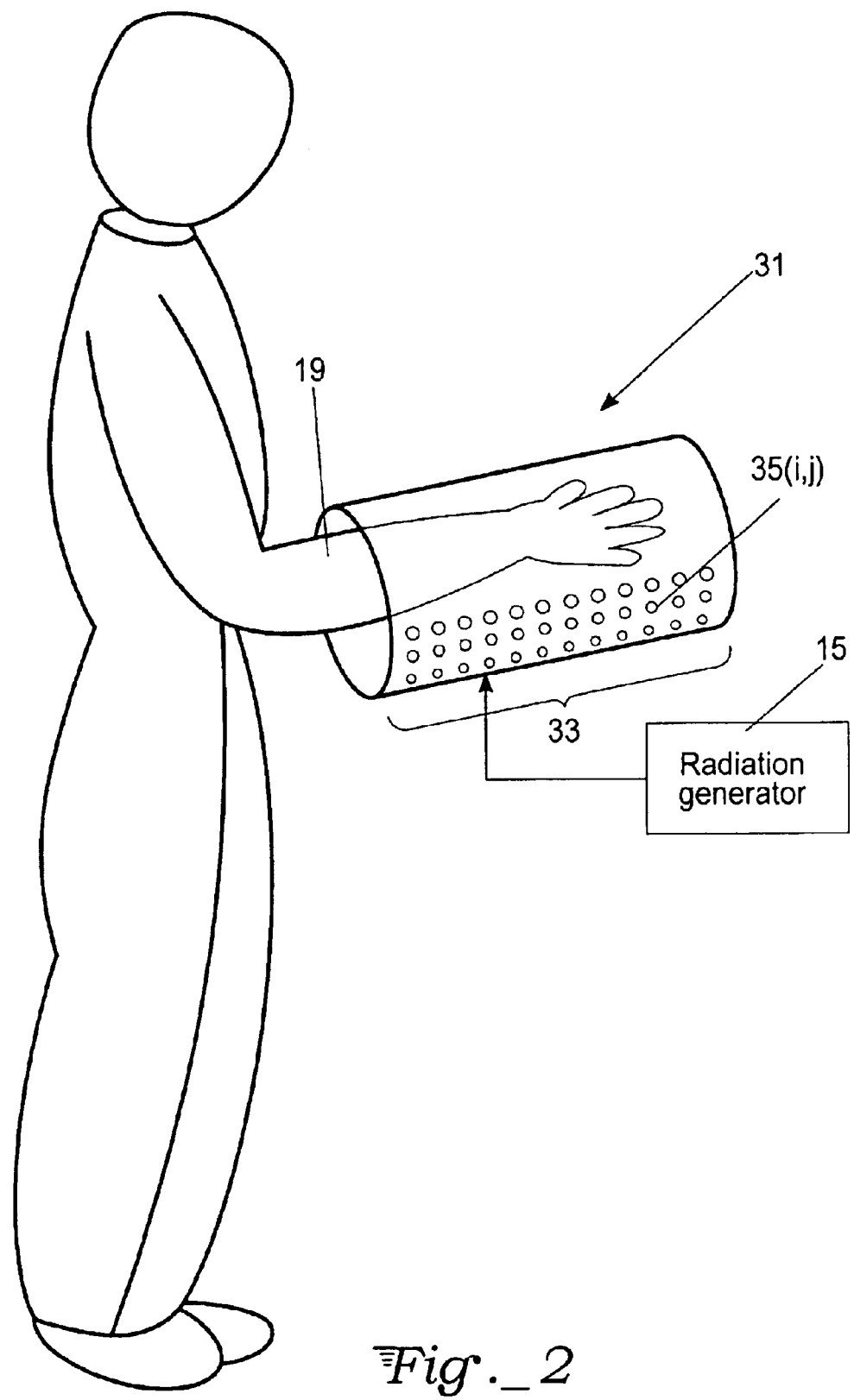

In one mode of operation, a flexible light delivery wrap 31, illustrated in FIG. 2, is connected to the radiation generator 15 in FIG. 1 and is wrapped around (a portion of) a toe, a foot, an ankle, a leg, a thigh, a hip, a torso, a shoulder, an arm, an elbow, a forearm, a wrist, a hand, a finger, a neck and a top portion of a head or other body appendage of the patient. The light delivery wrap 31 includes a rectangular, triangular, polygonal, ovular or other array 33 of light delivery elements $35(i,j)$ ($i=1, 2, \ldots, J1; j=1, 2, \ldots, J2; J1>1; J2>1$) that are individually activated in a timed sequence that may be the same, or different, for each light delivery element. In a first version, where the array 33 is rectangular or triangular, each row of light delivery elements $35(i,j)$ ($i=1, 2, \ldots, J1$; j fixed) is activated and is deactivated as a unit. In a second version, where the array is rectangular or triangular, the light delivery elements $35(i,j)$ ($i=1, 3, 5, \ldots$; j fixed) and $35(i,j)$ ($i=2, 4, 6, \ldots$; j fixed) are activated and are deactivated as separate units. Other patterns for light delivery activation and deactivation can also be used, depending upon the effect desired. Alternatively, the light delivery wrap 31 may be configured to enclose the entire body, or a substantial portion thereof. Preferably, this entire-body wrap does not enclose the patient's head, for which an independently controlled light delivery wrap, 41 and/or 51 (shown in FIGS. 3 and 4) is provided.

Figure 3:
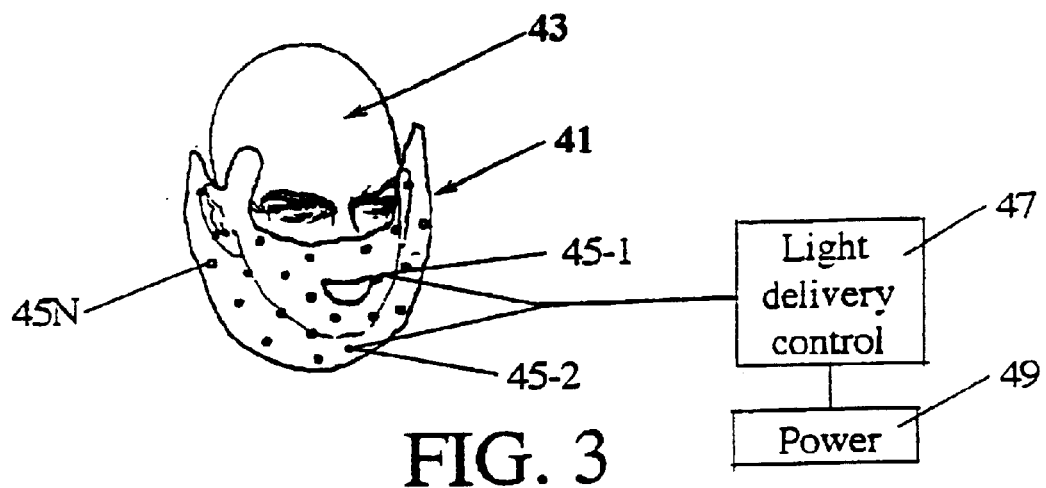

FIG. 3 illustrates a modular light delivery wrap 41 for a lower portion of a patient's head 43. The wrap 41 includes J light delivery elements 45-$j$ ($j=1, 2, \ldots J$; $J≧2$) whose positions can be adjusted to a location closer to, or further from, the patient's head 43. The light delivery wrap 41 also includes a light delivery control module 47 and a suitable power supply 49. The light delivery elements 45-$j$ can be made individually activatable (on/off) and can be individually activated within one or more time intervals. Thus, for example, a light delivery element 45-$j$1 may be moved to a position within 1–10 cm of a portion of a patient's face that has a discoloration (e.g., based on a medical condition), the light delivery element can be rendered activatable, and the light delivery element can be activated (pulsed or continuous mode) for a sequence of selected time intervals, for example, 40 sec per minute with a 10–90 percent duty cycle. The wrap 41 has also been used successfully for acne reduction, for scar reduction and for stress relief for one or more body components.

Figure 4A:
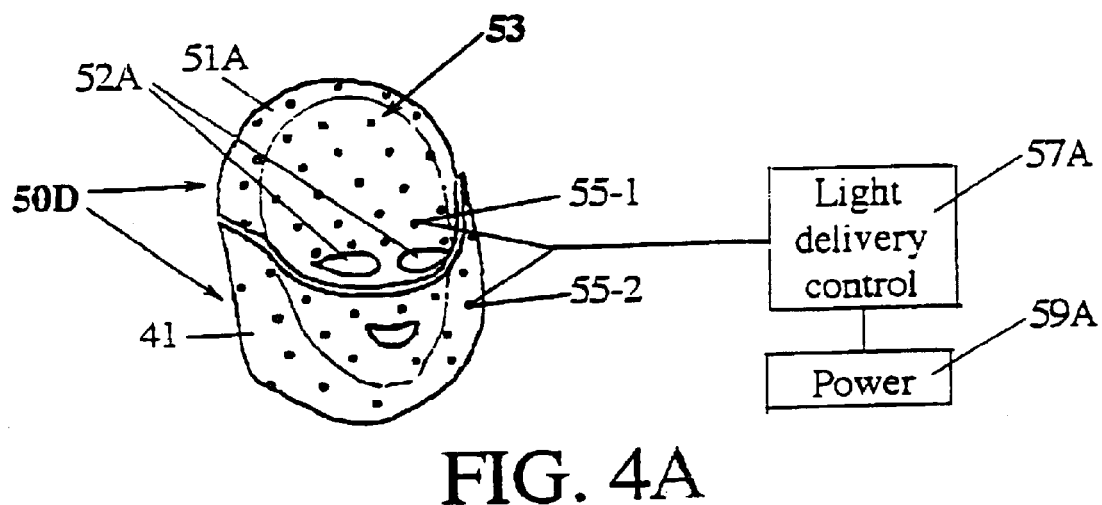

FIG. 4A illustrates a modular light delivery wrap 50A that combines the lower portion light delivery wrap 41 shown in FIG. 3 with a second light delivery wrap 51A that covers part or all of the upper portion of a patient's head 53. Optionally, each of the light delivery wraps, 41 and 51A, includes one or more light delivery elements 55-$j$ ($j=1, 2, \ldots$). Optionally, the second light delivery wrap 51 includes one or more apertures 52A in the wrap for the patient's eyes so that an eye is not subjected to direct illumination by a light delivery element 55-$j$. The light delivery wrap 50 also includes a light delivery control module 57 and a suitable power supply 59. The wrap 50: (1) provides a combination of two or more light delivery wrap components, here 41 and 51; (2) optionally provides an intra-aural mechanism for the interior of a patient's mouth or other cavity; (3) allows adjustment of a distance between at least one light delivery element 55-$j$ ($j=1, 2, \ldots$; $J≧2$) and an adjacent portion of the skin of a patient; (4) provides individual activation of light delivery elements so that one or more elements can be activated (turned on intermittently) and one or more other elements can be deactivated; and (5) provides adjustable light activation interval and dark field interval lengths (e.g., 0.1–1 sec) and adjustable duty cycles (e.g., 10–90 percent).

Figure 4B:
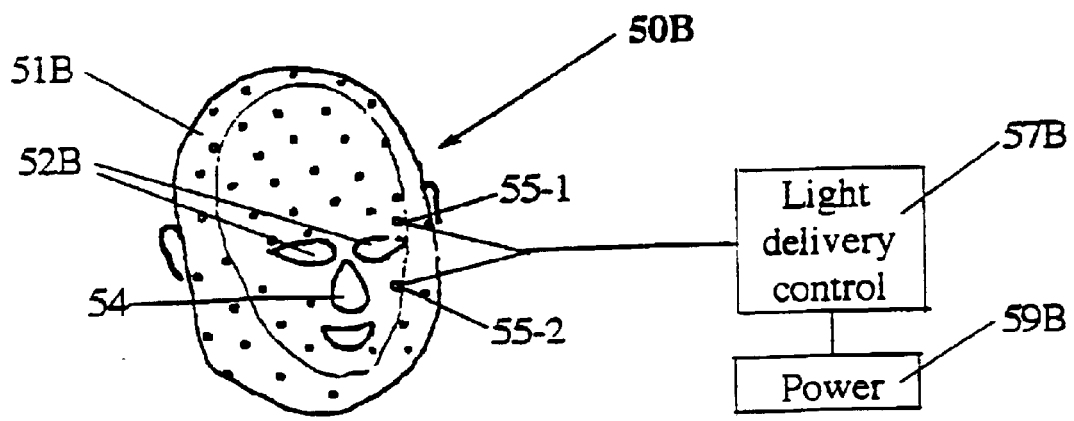

FIG. 4B illustrates a one-piece light delivery system 50B that covers most or all of the patient's face with a light delivery wrap 51B. Optionally, the light delivery wrap 51B includes one or more of an eye aperture 52B, a nose aperture 56B, a mouth aperture and an ear aperture (not shown) so that an eye and/or nose and/or mouth and/or ear is not subjected to direct illumination by a light delivery element 55-$j$. The light delivery system 50B also includes a light delivery control module 57 and a suitable power supply 59.

FIG. 5 illustrates a modular light delivery module 61 for the interior of a patient's mouth 63. The wrap 61 includes J light delivery elements 65-$j$ ($j=1, 2, \ldots$; $J≧2$) whose positions can be adjusted to a location closer to, or further from, the patient's mouth 63. The light delivery module 61 also includes a light delivery control module 67 and a suitable power supply 69. The light delivery elements 65-$j$ can be made individually activatable (on/off) and can be individually activated within one or more time intervals, as in the light delivery wrap 41 or 51 shown in FIG. 3 or FIGS. 4A/4B. The light delivery module 61 can be placed adjacent to the patient's teeth and/or gums within the mouth 63 and activated one or more times within a time interval to suppress or eliminate the growth or presence of dental caries, root regeneration, loose teeth or other dental diseases, or the presence of diabetes. One or more light delivery elements 65-$j$ can also be positioned near, and directed at, the roof of the patient's mouth 63 to irradiate and suppress growth of a bacterial or viral disease associated with the mouth interior, to support or boost the immune system, or to regenerate or maintain desirable reactions within the body. Optionally, the light delivery module 61 can be inserted into the mouth in a deflated condition, inflated for use on the mouth, then deflated for removal from the mouth. *Optionally, the light delivery module 61 is flexible so that its shape can be molded or reformed to fit the shape of the mouth interior.

FIG. 6 illustrates another shape, an egg-shaped or spheroidal light delivery module 71, having J individually activatable light delivery elements 75-$j$ ($j=1, 2, \ldots$; $J≧2$), connected to a light delivery control module 77 and to a suitable power supply 79. The light delivery module 71 may have any of a range of sizes. The light delivery module 71 may be a prolate spheroid with a≈2 cm minimum diameter and b≈4 cm maximum diameter, which is slipped into and out of a patient's mouth. The light delivery module 71 is optionally inserted into the mouth in a deflated condition, inflated for use in the mouth, then deflated for removal from the mouth.

FIG. 7 illustrates a tube-shaped or prolate spheroid light delivery module 81 having J individually activatable light delivery modules 85-$j$ ($j$=1, 2, ..., J; J≧2), connected to a light delivery control module 87 and to a suitable power supply 89. The light delivery module 81 has a transverse diameter D (small or large) that is suitable for insertion of the module into the vaginal or urethral or other reproduction cavity of a female or male and is preferably arranged so that the module can be inserted in a deflated state and subsequently inflated by a suitable amount for therapy, then deflated for removal. Alternatively, the light delivery module 81 is elastic and easily compressible to allow insertion and removal of the module in a partly compressed state. The light delivery module 81 is suitable for treatment or reduction of female or male genital disorders, such as genital herpes, yeast infections, prostate problems, post-surgical stimulations, hemorrhoids and the like. Preferably, most or all light delivery modules 85-$j$ are located at one end of the light delivery module 81.

Figure 8:
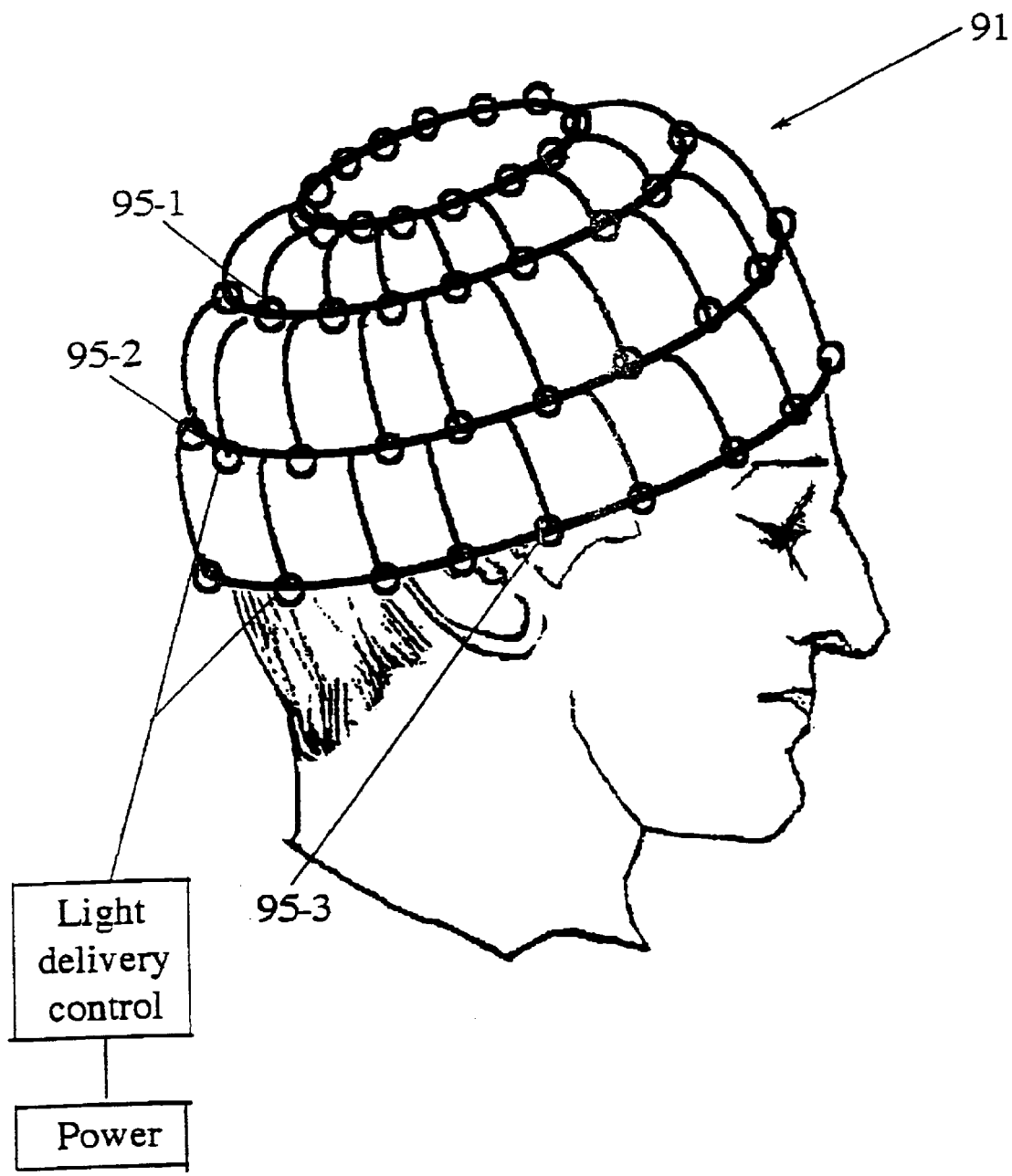

FIG. 8 illustrates a light delivery wrap 91 in the form of a hair net, upper head covering or similar configuration having a grid-like construction upon which J light delivery elements 95-$j$ ($j$=1, 2, ..., J; J≧2) are mounted. The light delivery elements 95-$j$ are connected to a light delivery control module 97 and a suitable power supply 99. The light delivery wrap 91 is useful for treating disorders of the scalp, the hair follicles and/or the ears of a patient's head, and in performing photo-acupuncture at one or more head meridians.

*The hair net, head covering or hat 91 shown in FIG. 8 can be reformed and extended, as an open format light delivery wrap, to be wrapped around a toe, a foot, an ankle, a leg, a thigh, a hip, a torso, a shoulder, an arm, an elbow, a forearm, a wrist, a hand, a finger, a neck or a portion of a head., to provide light therapy to a selected body part. The light delivery control module for the light delivery wrap, such as the hair net 91, can be arranged to be worn on the patient's waist or neck. This open format light delivery wrap can be worn inside the patient's clothes, if desired.

Figure 9:
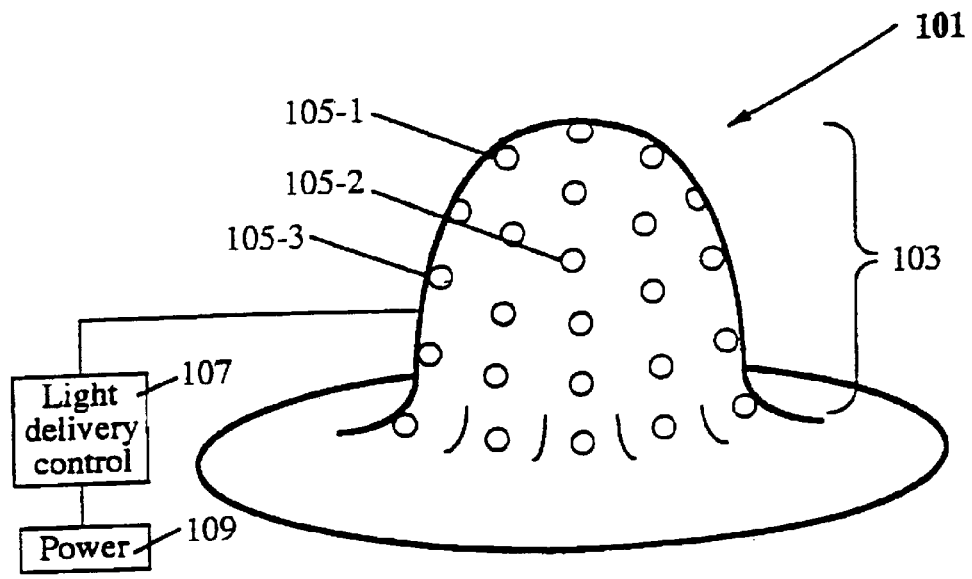

FIG. 9 illustrates a light delivery wrap 101 in the form of a hat or head covering, preferably made of soft, pliable fabric, having a grid-like construction upon which light delivery elements 105-$j$ ($j$=1, 2, ..., J; J≧2) are mounted. Optionally, the head covering 101 is made of an elastic material so that a portion 103 of the covering can be stretched and positioned contiguous to the wearer's head, thereby irradiating adjacent regions of the wearer's head. The light delivery elements 105-$j$ are connected to a light delivery control module 107 and a suitable power supply 109. The light delivery wrap 101 can be worn for general living activities without interfering with those activities. Optionally, in use of the apparatus illustrated in FIG. 8 or 9, back support and/or torso support for the user is provided for treatment and/or post-treatment recovery.

Figure 10:
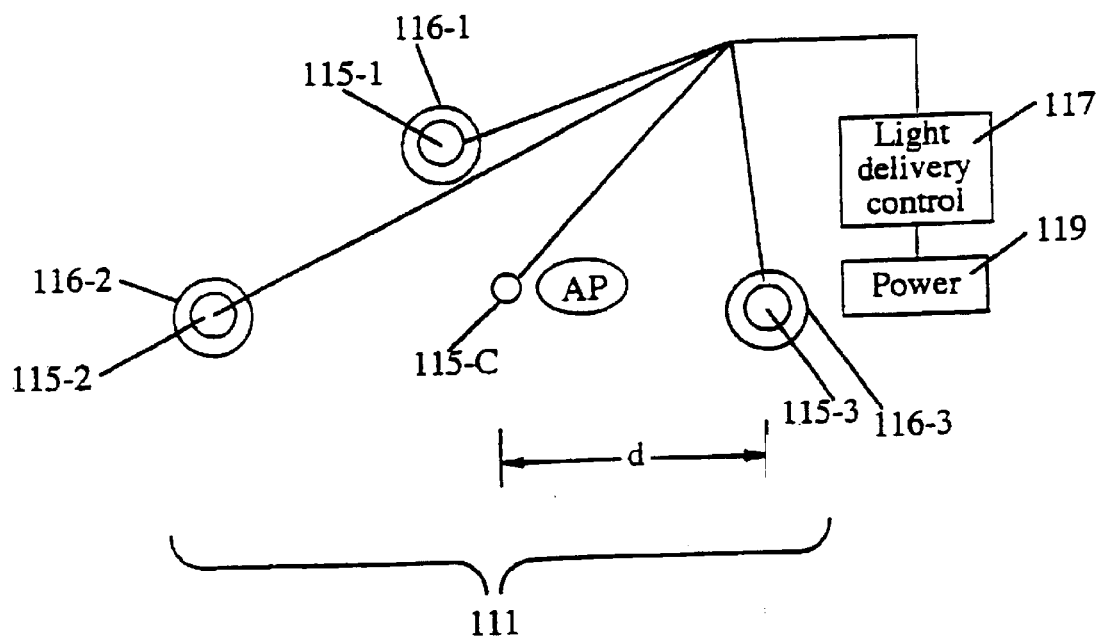

FIG. 10 illustrates a light delivery module 111 for placement on a portion of a patient's skin, as a substitute for, or supplement to, acupuncture treatment. The light delivery module 111 includes one, two, three or more peripheral light delivery elements 15-$j$ ($j$=1, 2, 3, ...) surrounding and spaced apart (preferably by 0.5–2 cm) from a central light delivery element 115C that is used to position the module 111 and/or to deliver additional light to a selected site. The central light delivery element 115C may deliver light in the same wavelength range(s) as is delivered by the peripheral light delivery modules 115-$j$ or may deliver light in one, two or more wavelength ranges that are different from the wavelength range(s) delivered by the peripheral light delivery elements 115-$j$. Preferably, the wavelength range for the central light delivery module 115C includes at least a portion of the visible spectrum. The light delivery wrap 111 also includes a light delivery control module 117 and a suitable power supply 119.

The central light delivery module 115C in FIG. 10 is preferably positioned at or adjacent to a known or suspected acupuncture point or meridian AP. The peripheral and/or central light delivery elements, 115-$j$ and/or 115C, are activated and deliver light in one or more selected wavelength ranges to the acupuncture meridian and surrounding tissues, to supplement or replace a conventional acupuncture treatment that uses needles. One advantage of replacement of conventional acupuncture treatment by light therapy, delivered to the same site(s), is that the patient's skin need not be mechanically punctured. Use of light therapy (1) avoids possible introduction of bacteria or other organisms at an acupuncture site, (2) avoids allergic and other similar reactions to the material (metals, etc.) used in acupuncture tools and (3) allows simultaneous delivery to multiple sites.

The light delivery elements 115-$j$ in the light delivery module 111 can be supplemented by one or more static or time-varying magnetic field sources 116-$j$, as indicated in FIG. 10; the (peak) magnetic field strength can range from 100–10,000 Gauss, or higher if desired. A static and/or time-varying magnetic field having an associated frequency f=1–$10^4$ Hz, or higher if desired, is optionally provided as part of the light-plus-magnetic field therapy. An acupuncture channel may preferentially transport a magnetic field in somewhat the same manner that a light beam is believed to be preferentially transported by an acupuncture channel.

*The light delivery module 111 can be "ganged" together with one or more additional, similar light delivery modules in a modularized approach to cover a surface region of the patient's body larger than can be covered by a single light delivery module. Optionally, the light delivery control module 117 for two or more individual light delivery modules are integrated so that a single light delivery control module 117 controls the light sequences and wavelengths and/or magnetic field frequencies f delivered by a group of two or more ganged-together light delivery modules 111.

Light therapy may also be applied in the form of a modular electronic or electromagnetic or photonic band-aid 121, illustrated in FIGS. 11A–11D and 12, and including one, two or more modular band-aid components, 122-1, 122-2, etc. that are optionally disposable. Each band-aid component, 122-1 and 122-2, includes an adhesion mechanism 123 (adhesive, velcro, mechanical wrap-around, hooks, etc.) that adheres to a selected portion of a patient's skin or clothes, and includes J light delivery elements 125-$j$ ($j$=1, 2, ...; J≧2) that are selectively activated by a light delivery control module 127 and a suitable power supply 129. Optionally, the control module 127 and/or power supply 129 are miniaturized and self-contained and are worn or carried on the patient's body 126. The band-aid 121 may be applied to provide a "fast start" for a surface or subsurface healing or other treatment process (e.g., for emergency use) or may be applied longer term as an integral part of a total healing process or for body component maintenance.

Figure 11:
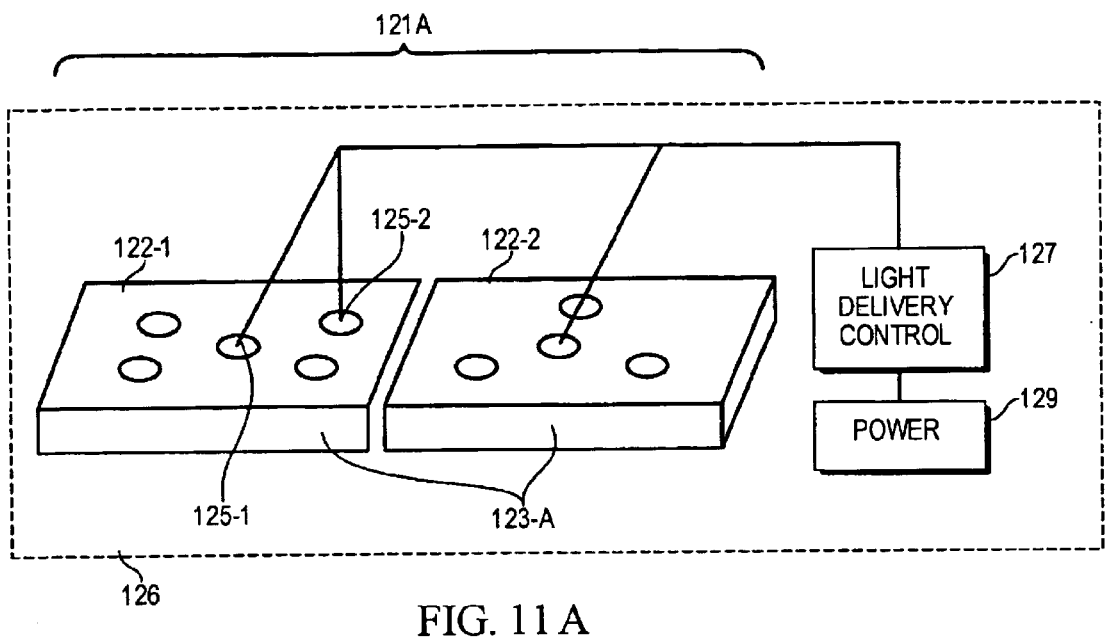
Figure 12:
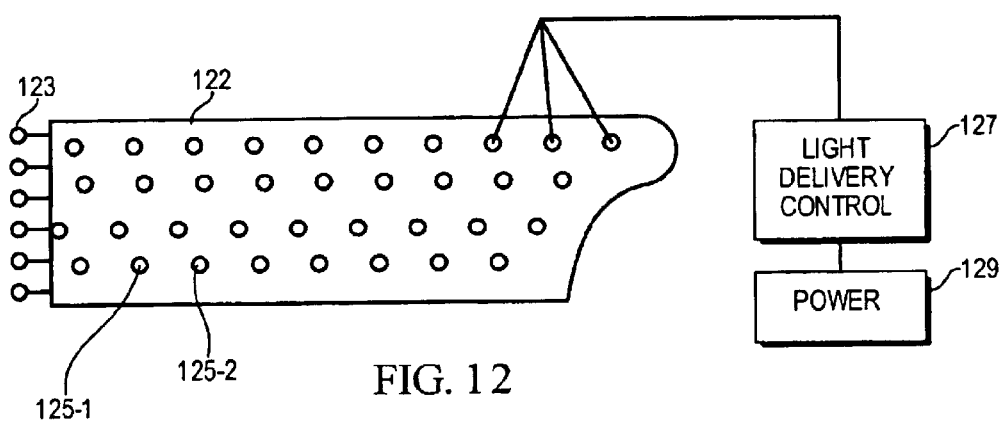
Figure 11:
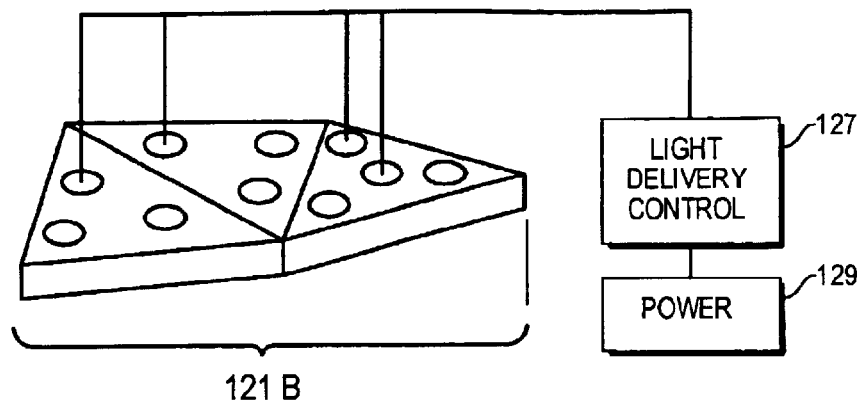
Figure 11:
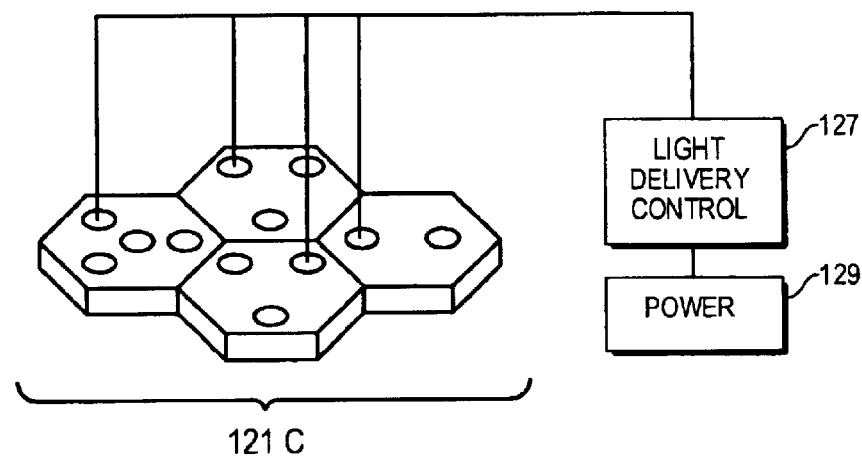
Figure 11:
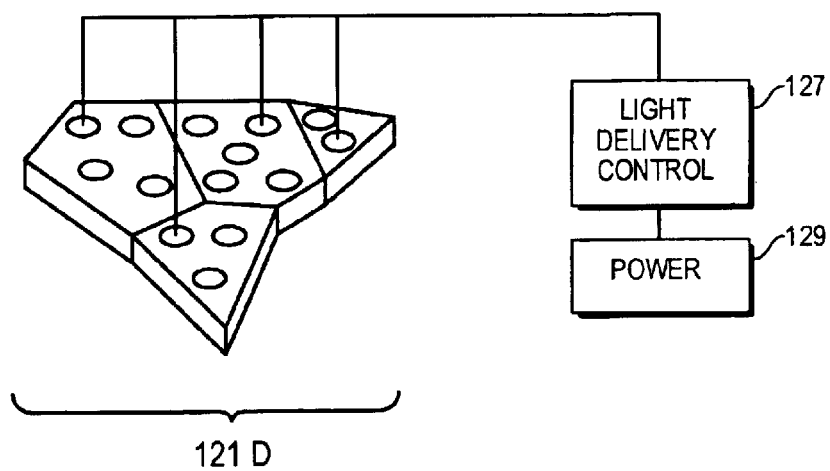

*In the embodiment shown in FIG. 11A, the individual photonic band-aid components 122-$j$ are rectangular. FIGS. 11B, 11C and 11D illustrate suitable other shapes for band-aid components, including regular triangles, regular hexagons and non-regular polygons. Two or more band-aid components or varying shapes can be used to cover a larger surface region or a surface region of irregular or unusual shape, or to replace a photonic band-aid component that is no longer operational. One or more of the light delivery elements 125-$j$ shown in FIG. 11A can be supplemented with a magnetic field source, such as the magnetic field sources 116-$j$ shown in FIG. 10.

*Where a photonic band-aid is to be worn for more than a certain time interval, such as more than 8 or 16 or 24 hours, the associated power supply 129 is preferably rechargeable so that the module 121 can be renewed by recharging the battery in place. In this situation, a power supply 129 is optionally provided with a first power supply module that is presently being used and a second, adjacent power supply module that is not presently being used and that can be recharged in parallel with present use of the first power supply module, without requiring removal of the photonic band-aid from service.

Figure 13:
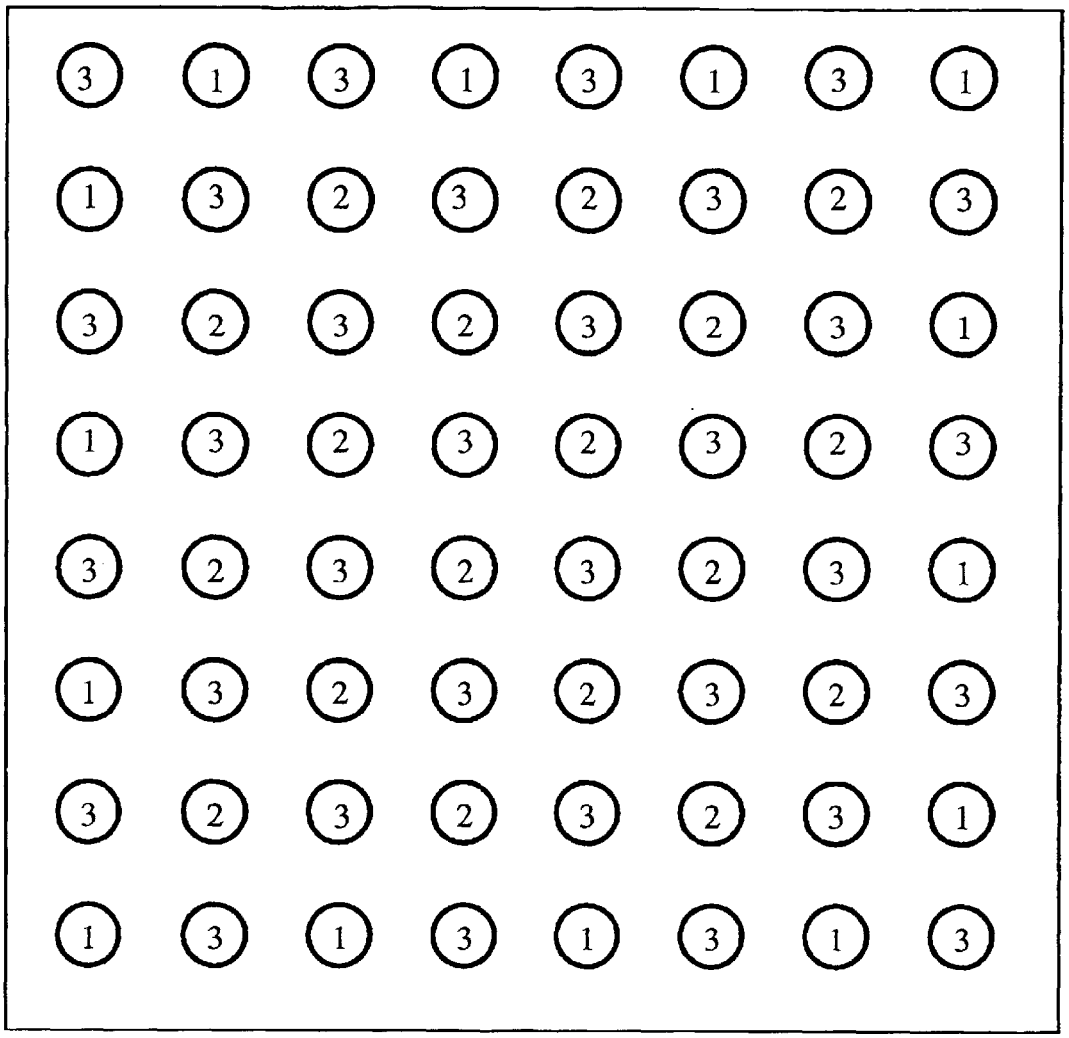
FIG. 13 schematically illustrates a suitable pattern of light sources for different wavelengths.

FIG. 13 illustrates a suitable light delivery pattern, in which selected light sources (e.g., light emitting diodes) deliver light in one, two, three or more selected wavelength ranges.

The preferred frequencies of application of the magnetic field are the following: (i) 1.7 Hz and/or 8 Hz (primarily for general stress reduction or relief); (ii) 4 Hz and/or 80 Hz (primarily for relief of sports-related stress); (iii) around 266 Hz (primarily for regeneration or cosmetic purposes); and/or (iv) other low frequencies suitable for stress relief, component regeneration and/or maintenance of beneficial chemical or physical reactions. For dental applications, the preferred frequencies of application are similar but further include a frequency of application around 666 Hz for regeneration. These treatments are normally applied for time intervals of 15–45 minutes but can be applied for shorter or longer time intervals as well.

Figure 14A:
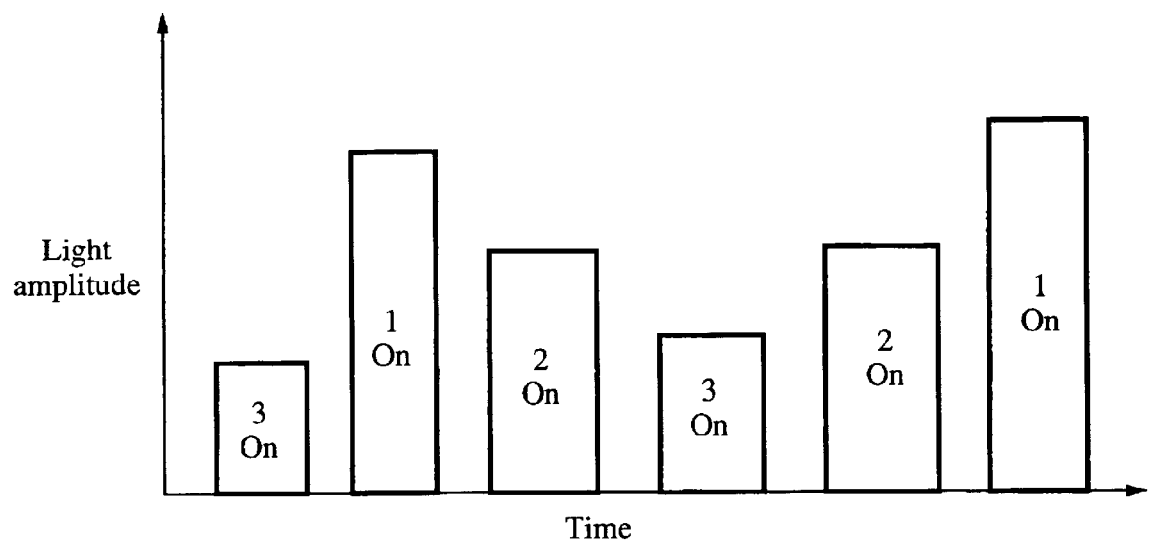
FIGS. 14A and 14B graphically illustrate time intervals for irradiation using different wavelength ranges according to two embodiments of the invention.
Figure 14B:
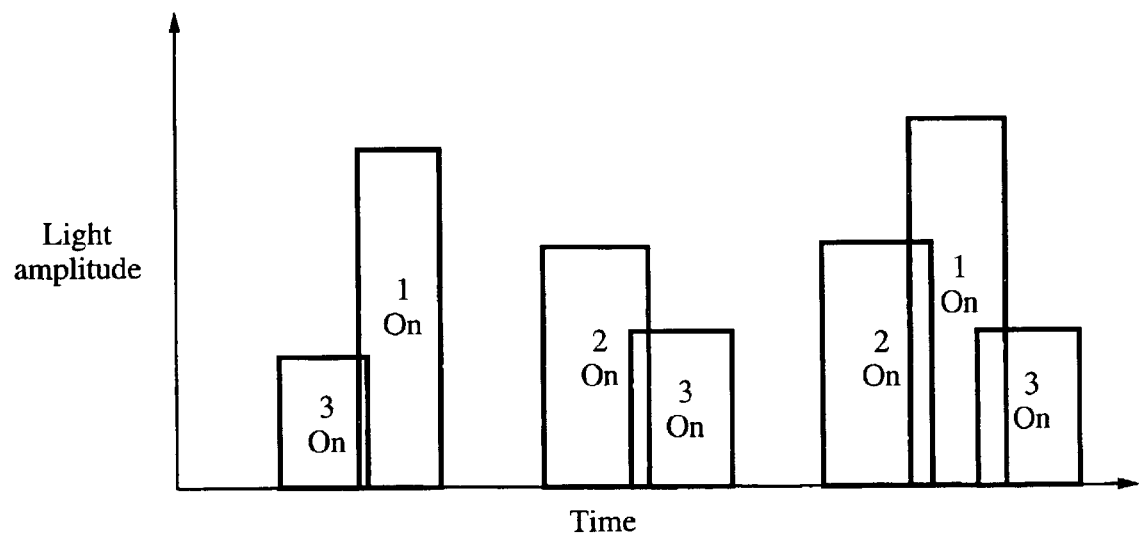

In a preferred embodiment of the invention, the light sources for the different wavelength ranges provide light in different time intervals, with or without a dark field time interval imposed between two consecutive irradiation time intervals. FIG. 14A is a graphical view of time intervals during which the first, second and third light sources (1), (2) and (3) are activated in a non-overlapping manner. FIG. 14B is a graphical view of a second version, in which the light sources (1), (2) and (3) are activated in selected overlapping time intervals. More generally, N sets of independently activatable light sources (N=1, 2 or 3 in FIG. 13) are provided, and N wavelength ranges are chosen within the visible, near-infrared and mid-infrared wavelengths.

Each light delivery element (e.g., 35($i,j$) in FIG. 2) may deliver light in one or more selected wavelength ranges, when this element is activated, and adjacent light delivery elements may deliver the same, or different, wavelength ranges. In a preferred embodiment, each light delivery element delivers one or more selected ranges of light wavelengths. More generally, light in any of N color ranges can be delivered (e.g., N=7), and the color ranges are chosen according to the treatment or therapy to be provided and the chosen color ranges can be changed as a treatment or therapy session proceeds.

*It is often appropriate to deliver light in two, three or more wavelength ranges in a coordinated manner, either simultaneously, or in overlapping or non-overlapping but adjacent time intervals. Light emitting diodes (LEDs) are being developed that allow generation and delivery of light in two or three separate wavelength ranges simultaneously. For example, wavelength intervals including two or more of the following wavelengths have been found to be useful for healing and/or regeneration purposes: $\lambda$=470 nm (useful for treating Alzheimer's disease), 550 nm, 637 nm (useful for skin or surface healing), 666 nm, 890 nm and 905 nm. Anticipated synergistic effects through substantially simultaneous application of two or more of these wavelengths include the following: _____. Other attractive applications include treatment of bed sores, relief from winter depression in sun-deficient climates, internal body healing and enhancement of generation of human growth hormone (HGH) in some persons (up to a 148 percent increase in HGH with a 30-day light therapy treatment three times per week). Preferably, the light therapy treatment is applied two or three times per week during an initial stage, followed by a maintenance phase of one application per week.

Figure 15:
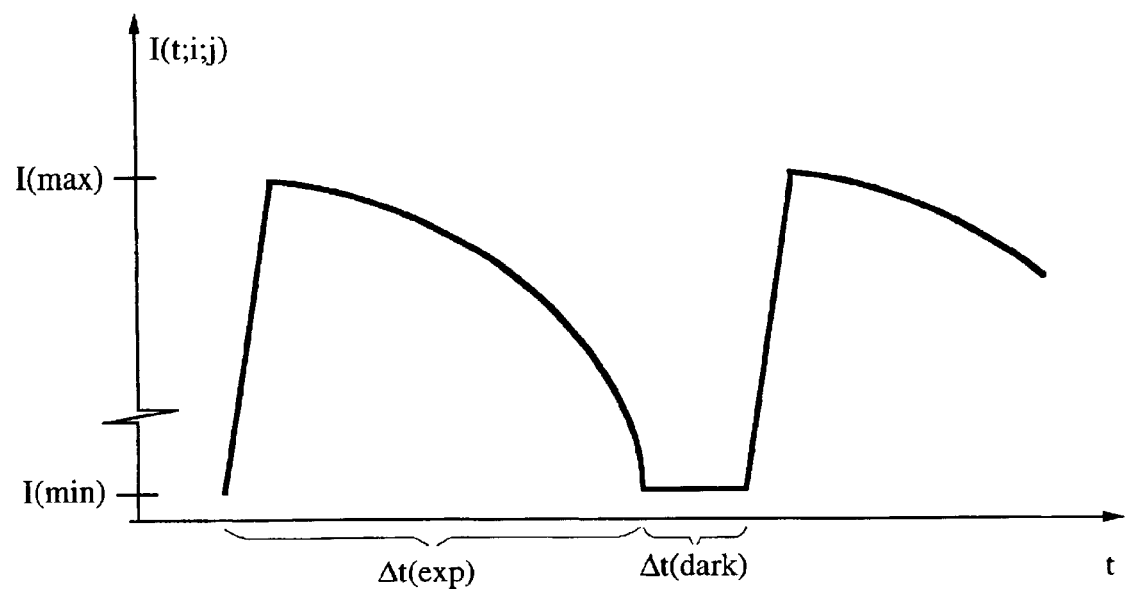
FIGS. 15, 16 and 17 illustrate suitable light intensity patterns versus time for delivery of radiation according to the invention.
Figure 16:
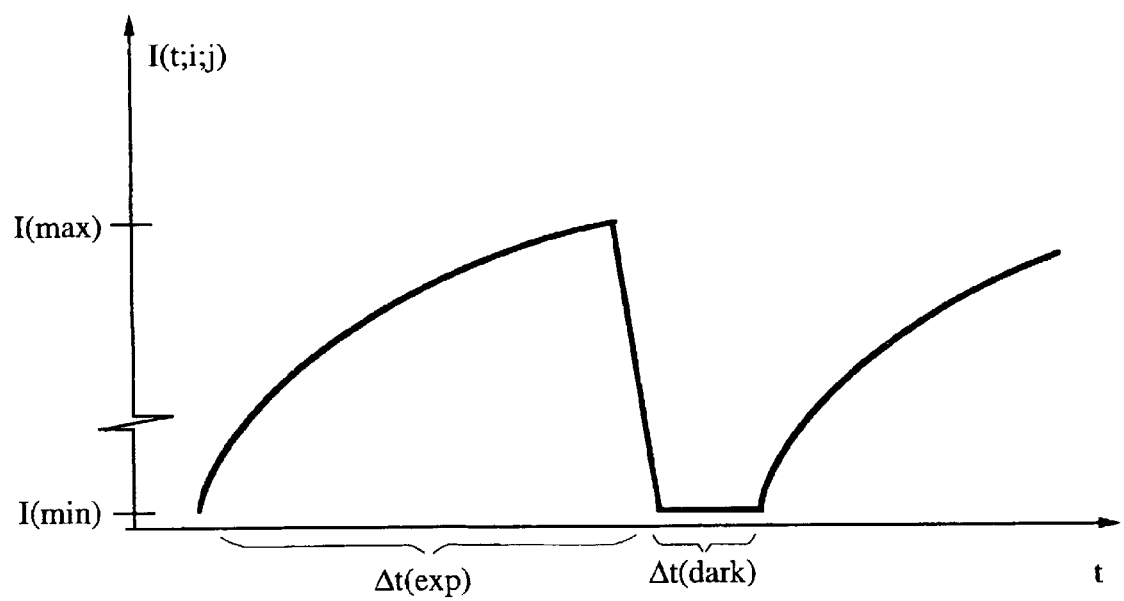
Figure 17:
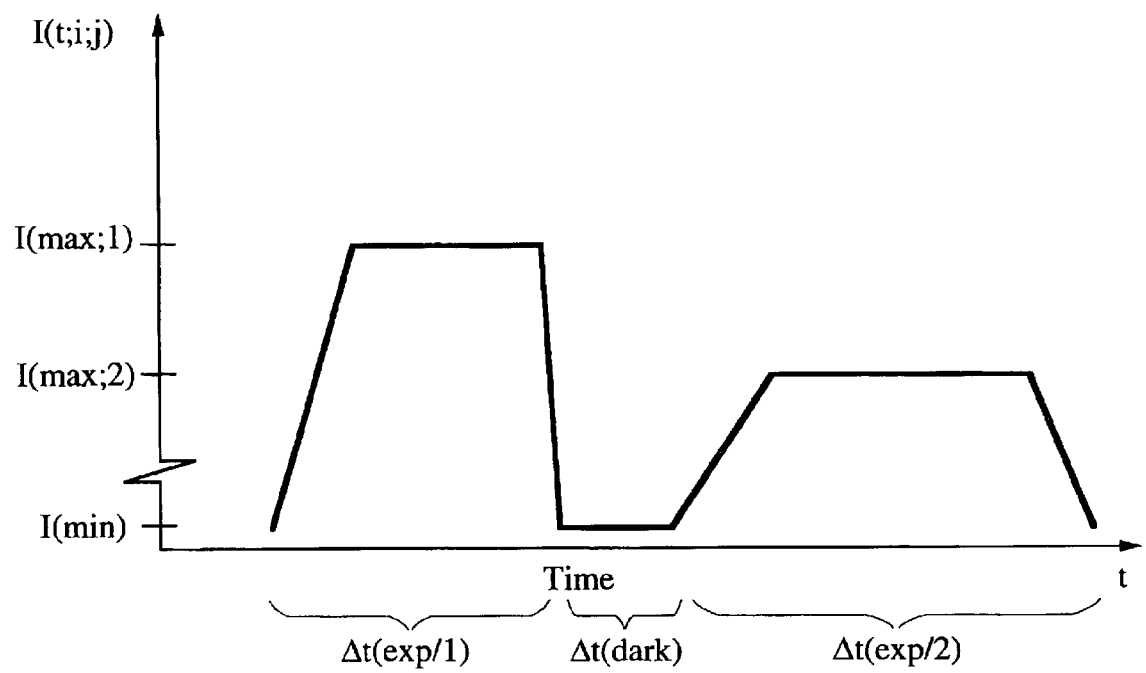

FIGS. 15, 16 and 17 illustrate representative light intensity patterns of light activation (exposure interval) and deactivation (dark field interval) that can be used for the individual light elements 35($i,j$) in FIG. 2. In FIG. 15, the light intensity I(t;i;j) is (substantially) 0, then rises quickly to a maximum value I(max), then decreases monotonically to a lower value I(min) over an exposure time interval of length $\Delta$t(exp), then goes to a (substantially) zero value for a dark field time interval of length $\Delta$t(dark), then repeats this pattern at least once.

In FIG. 16, the light intensity I(t;i;j) rises monotonically from a (substantially) zero value to a maximum value I(max), then falls quickly to a minimum or zero value I(min), over an exposure time interval of length $\Delta$t(exp), then goes to a (substantially) zero value for a dark field time interval of length $\Delta$t(dark), then repeats this pattern at least once.

In FIG. 17, the light intensity I(t;i;j) rises to a first maximum value I(max;1), optionally continues at or near that level for a first selected illumination time interval of length $\Delta$t1, falls to a first lower value I(min;1), goes to 0 for a dark field time interval of length $\Delta$t(dark), rises to a second maximum value I(max;2), optionally continues at that level for a second selected illumination time interval of length $\Delta$t1, falls to a second lower value I(min;2), then goes to 0. The maximum intensities I(max;1) and I(max;2) may be the same or may differ, the minimum intensities I(min;1) and I(min;2) may be the same or may differ, and one or both of the minimum intensities I(min;1) and I(min;2) may be 0. Light intensity patterns other than those shown in FIGS. 14, 15 and 16 can be used.

Each photon delivered to the vicinity of the body component 19 (FIG. 1) is intended to produce one or more (preferably many) free electrons through photoelectric absorption and/or Compton scattering of the photon in its peregrinations through the body component and surrounding material. I have found, by analogy with the Einstein photoelectric effect in a metallic or crystalline material, that the photon energy E must be at least a threshold value E(thr), which lies in a range of about 0.8–3.1 eV, depending upon the atomic and/or molecular constituents of the selected body component and surrounding material, in order to produce at least one free electron as the photon undergoes scattering within the body. A photon with a wavelength $\lambda$=500 nm has an associated energy of 2.48 eV, for example.

Figure 18:
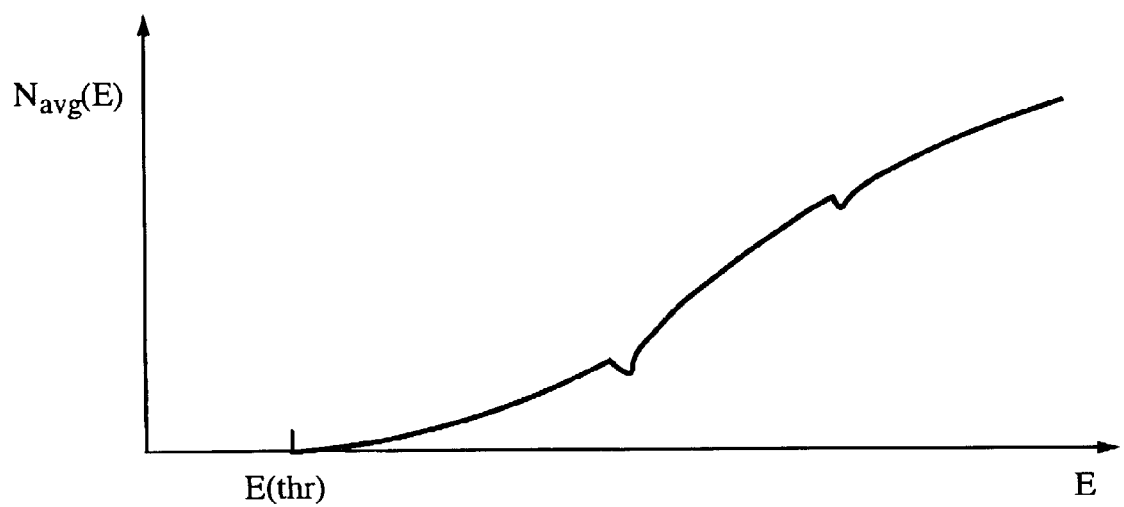
FIG. 18 is a representative graphical view of an average number of free electrons produced by an incident photon with a specified energy E.

Not all photons with energies E just above the threshold value E(thr) will produce a free electron. A graph of average number $N_{avg}(E)$ of free electrons produced for a given incident photon energy E might resemble the graph in FIG. 18. This graph is similar to a graph of average number of free electrons produced by a photon incident on a metallic or crystalline material according to the Einstein model.

Another important parameter is the rate r at which energy (or photons) is delivered to a unit area (e.g., over 1 cm$^2$) of body surface per unit time (e.g., in 1 sec), during an exposure time interval. Our experiments indicate that energy density rates r in a range 0.0013 Joules/cm$^2$/sec$\leq$r$\leq$0.02 Joules/cm$^2$/sec, averaged over a time interval of 5–45 min, is an appropriate range for many body components. Delivery of energy at a rate lower than about 0.0013 Joules/cm$^2$/sec will have some effect but will require much longer radiation application times than a typical application time of 5–45 min. Delivery of energy at a rate greater than about 0.02 Joules/cm$^2$/sec may saturate the body's ability to distribute the photon energy and may produce burns, ionization or other undesired local sensitization of the body. The peak light intensity I(t;i;j), shown in the examples of FIGS. 13, 14 and 15, will determine, or will be determined by, the energy rate r.

Another important parameter is accumulated energy E(accum) delivered per unit area for the session in which radiation is applied. Our experiments indicate that an accumulated energy density range of 2.5 Joules/cm$^2$$\leq$E(accum) $\leq$20 Joules/cm$^2$ is an appropriate range for many body components.

Figure 19:
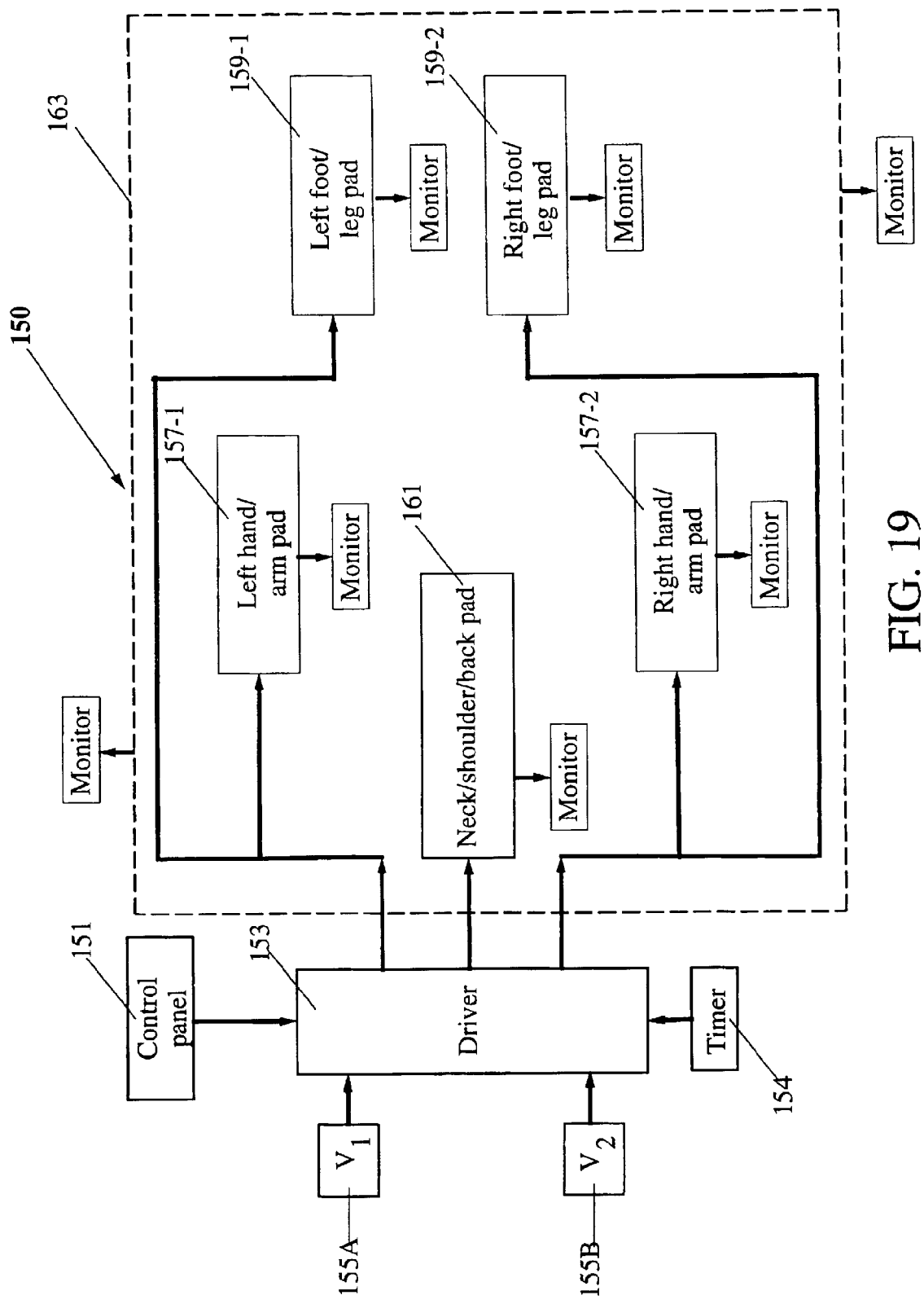
FIG. 19 is a schematic view illustrating apparatus that can be used to practice the invention.

FIG. 19 schematically illustrates apparatus 150 that can be used to practice the invention for a patient's whole body, or parts thereof. A control panel 151 controls the exposure time intervals, the dark field time intervals, the maximum intensity(ies), the particular intensity pattern(s) to be applied, the wavelength or frequency range(s) to be applied, target body component(s) and/or other relevant parameters, through control panel output signals delivered to a driver module 153. The driver module receives timing signals from a timer module 154 and receives electrical power (preferably regulated power) from one or more voltage sources, 155A and/or 155B, that deliver voltage(s), V1 and/or V2, or electrical current. At least one of the control panel 151 and the driver module 153 includes a computer to process information and/or commands needed to provide appropriate light wavelengths in the appropriate time intervals according to the invention. The driver module 153 delivers power to one or more of a left hand/arm exposure pad 157-1, a left foot/leg exposure pad 159-1, a right hand/arm exposure pad 157-2, a right foot/leg exposure pad 159-2 a neck/shoulder(s)/back exposure pad 161, and/or a light exposure canopy 163 covering part or all of a patient's body, each of which has an optional associated cumulative exposure monitor and/or exposure rate monitor connected to the corresponding exposure pad or exposure canopy. Optionally, one or more of these exposure pads may have its own electrical power supply, received directly from the driver module 153. The exposure pads are individually controlled and can deliver different (or the same) exposure patterns and different (or the same) wavelength ranges to target body components associated with the different exposure pads, in the same time intervals or in different time intervals. In some situations, it is appropriate to provide at least two voltages sources, such as V1=5 volts and V2=12 volts.

I have found that insertion of a dark field time interval between two consecutive continuous exposure time intervals is useful in allowing the irradiated portion of the body to re-establish local equilibrium before the next pulse of photons arrives. The time interval required for re-establishing local equilibrium appears to vary from 0.1 sec to about 1 sec, depending upon variables such as the energy rate r, the accumulated energy E(accum) and the selected body component(s) irradiated. If the dark field time interval has a length less than a threshold value $\Delta$t(dark) (including a situation where no dark field interval is present), the additional photons delivered may encounter a body environment that is not at or near equilibrium and that "channels" these photons in particular directions or into particular reaction channels, which is generally undesirable. Where two consecutive exposure time intervals are separated by a dark field time interval of length at least $\Delta$t(dark), the irradiated portion of the body is able to re-establish local equilibrium, or near-equilibrium, so that most or all photons within a given exposure time interval encounter substantially the same local environment, and a random or Monte Carlo type of photon scattering occurs within the next exposure time interval.

The free electrons thus produced ultimately come to equilibrium with the body component and adjacent material within the body, by attachment to a atom or molecule that can support attachment by another electron or by association with a assembly of substantially-free electrons that are weakly bound by the general electronic background of the local atomic and molecular constituents of the body. These equilibrated electrons have transferred substantially all their initial kinetic energy to one or more molecules in or adjacent to the body component, thus providing energy to promote certain healing processes in the body.

Phototherapy is the application of light from an artificial light source to stimulate or promote one or more therapeutic effects in the body of an animal. such as a human being. Photons from the, light source are absorbed by the body through the skin, through the eyes and through acupuncture points or meridians. Light absorbed through one or more acupuncture points is believed to be transported especially efficiently along channels, referred to as biologically closed electrical paths or "meridians", in the body, through a process similar to internal reflection of light in an optical fiber (whose refractive index is greater than the refractive index of the surrounding body material through which such a channel passes. These channels are believed to be connective tissue protein fibers having specialized optical properties, including refractive indices $\eta$ that are greater than the refractive indices $\eta'$ of surrounding tissues, organs and other body material (wherein $\eta'$(avg)$\approx$1.4).

Only light in certain wavelength ranges will be transported efficiently through these channels. Absorption of light transported in one or more of these channels has the potential to increase cell metabolism from a depressed state to a normal level. Light in the 600–800 nm wavelength range appears to be transported with little absorption or scattering within these channels. Sergei Pankratov, of the Institute for Clinical and Experimental Medicine in Novosibirsk, Russia, has reported that marked light transporting properties of some of these channels, which easily transport light into tissues deeper within the body, "Meridians Conduct Light", Raum und Zeit, vol. 35(88) (1991) pp. 16–18. A terminal on the skin of such a channel often coincides with an acupuncture point or meridian identified by Chinese physicians several millenia ago. In addition to its optical properties, a light transport channel has associated thermal properties, such as heat conductivity and heat capacity, that differ from those of surrounding tissues.

Phototherapy activates cell membranes within the body by increasing a membrane's natural electrical charge, sometimes referred to as "membrane capacitance." A body is, in a sense, "charged" with photons, and the body's natural electromagnetic field ("biofield") aids in organizing molecular structures in repair, regeneration and reproduction of cells and cell components and serves as a signal communication system in regulation of metabolic processes. The biofield may also serve as a power grid to provide electrical and/or chemical energy to drive and control biochemical and biophysical enzyme reactions that are part of a metabolic process. One such process is: (1) receipt and conversion of light in a channel; (2) activation of cell enzymes; and (3) enhanced production of adenosine triphosphate (ATP) from the activated enzymes, as the primary energy source for a body. Use of phototherapy to stimulate production and/or assimilation of human growth hormone (HGH) within the body is another attractive application.

One researcher, Tiina Karu has determined that light absorption by cellular structures enhances a number of cell-related activities: cell replication, cell metabolism, protein synthesis, ATP production, mitochondria replication, phagocytosis, and photodissociation of oxygenated hemoglobin (*The Science of Low-Power Laser Therapy*, Gordon and Breach, 1998, "Photobiology of Low Power Laser Effects", Health Physics, vol. 56, May 1989). Karu has also found that absorption of light affects tissue-related activities, including: capillary formation, parasympathetic nervous system stimulation, increased endorphin release, increased production and release of adrenal steroids, reduction in pain and in inflammation, reduction of tissue edema, immune system stimulation, enhanced fibroblastic production and collagen synthesis, and accelerated healing of wounds.

Several tests have been performed on a small group (27) of adult subjects that appeared to be representative of the adult population. Biological terrain assessment was performed to obtain a general understanding of certain internal elements of a body's control system, including analyses of blood, urine and saliva for the factors of pH (acid/alkali balance), rH2 (oxidative stress) and r (mineral content). About 81 percent of the test subjects showed a reduction in selected biological aging markers after a four week therapy session of twice-weekly treatments, with no plateau in such reduction during the therapy session; and 100 percent of the test subjects experienced a drop in rH2, indicating increased cellular absorption of electrons and higher ATP energy production.

An Endocrine Panel was performed on each test subject, measuring adrenal, gonadal and thyroid functions, as well as melatonin end human growth hormone (HGH) levels. All test subjects had significant improvements HGH levels after the four-week therapy session. Thyroid function improvement, as manifested by higher levels of active triodothyronine and melatonin secretion, was found in most test subjects.

A GENOX oxidative stress test, including 82 related assays that have some correlation with life expectancy, was performed initially (to provide a reference) and after the four-week therapy session. All test subjects showed increased ATP production.

An Immune Panel 2 was performed, measuring response of several immune functions to immune system stimulation. Interleukins and lymphokines, which regulate humeral and cell-mediated immune response, were improved, and numbers of T cell subsets increased, indicating improved T cell function.

Adrenal Stress Index (ASI) tests were performed to measure hyper- and hypo-adrenocortisol states, deregulation of the hypothalmic pituitary gland adrenal axis and intestinal secretory IgA, and a gliadin antibody test was performed. The ASI tests provide a measure of effects of chronic stress on organ reserve. Chronic stress often leads to a more catabolic state, with increased metabolic destruction. A significant reduction in cortisol, ranging from 23 to 81 percent, was found in the test subjects, indicating a reduction presence of the catabolic state.

DHEA/cortisol ratios were measured to evaluate the anabolic/catabolic state. Each test subject improved during the therapy session. Intestinal secretory IgA, which is a measure of mucosal immunity and has a low value where food allergies, chronic fungi and parasitic infections are present, was improved by 25 to 300 percent in the test subjects.

A urinary free radical test was performed to measure metabolites of lipid peroxidation in urine. Decreases of 33 to 66 percent in free radical generation were found in the test subjects, indicating a decreased likelihood of cardiovascular disease and stroke.

A heart rate variability (HRV) test, measuring beat-to-beat variability, was performed on each test subject in a sitting position and in a standing position. A strong correlation exists between high variability and cardiovascular problems such as coronary artery disease, heart attack, and prolonged recovery from such an attack. The test subjects consistently showed improvement in HRV, with no change in lifestyle or diet.

Blood pressure tests performed on the test subjects showed a 5–10 mm Hg drop in systolic pressure and 3–7 mm Hg drop in diastolic pressure, relative to blood pressure levels measured before the therapy session began. However, some of this improvement often disappeared after the therapy session ended and light therapy treatment had been discontinued.

Aqueous hydrogen peroxide production was measured before the therapy session began and after the four-week session ended. Aqueous hydrogen peroxides are free radical generators and oxidants used to fight infection and to support the immune system. A balance of oxidants and anti-oxidants is needed in the body. The test subjects consistently showed a significant reduction from pre-treatment levels, indicating the light therapy is not generating net gains in free radical populations.

Glutathione, red blood cell count and plasma were measured to evaluate anti-oxidant activity. Glutathione provides some of the most potent anti-oxidant reserves in the body. Levels of vitamin C, vitamin E, glutathione, beta-carotene, uric acid, albumin, ferritin, ceruloplasmin and transferin, which scavenge oxygen species of free radicals, were measured. Depletion of anti-oxidants is important in the ageing process and in associated diseases, such as arteriosclerosis, cancer, asthma, diabetes and immune deficiency diseases. The glutathione reserves continued to be regulated and were not depleted or interfered with during the therapy session.

What is claimed is:

1. A method of illuminating an animal's body, the method comprising:

positioning a light delivery module adjacent to a selected component of an animal's body, the module having first and second light delivery elements that can each be activated to intermittently illuminate the body component with light having at least two wavelengths;

exposing the body component to light from the first light delivery element of the light delivery module, the first element having a first selected range of wavelengths and a second selected range of wavelengths that does not substantially overlap the first range, for a first selected exposure time interval, and allowing light received in this first time interval to produce at least one free electron within or adjacent to the body component;

exposing the body component to light from the second light delivery element of the light delivery module, the second element having a third selected range of wavelengths and a fourth selected range of wavelengths that does not substantially overlap the third range, for a second selected exposure time interval, and allowing light received in this second time interval to produce at least one free electron within or adjacent to the body component, where the first and second exposure time intervals are spaced apart by a dark time interval having a selected length $\Delta t(\text{dark})$ that is at least about 0.1 sec; and allowing the at least one free electron produced during each of the first and second exposure time intervals to come to equilibrium with the body adjacent to or within the body component.

2. The method of claim 1, further comprising including in at least one of said first, second, third and fourth wavelength ranges at least one of the following wavelengths: 470 nm, 550 nm, 637 nm, 666 nm, 890 nm and 905 nm.

3. The method of claim 1, further comprising providing said light delivery module with a power supply system that comprises first and second independent power supplies, where the first power supply is capable of supplying power for operation of said light delivery module while the second power supply is being recharged.

4. The method of claim 1, further comprising providing said light delivery module with a light delivery wrap that is configured to be wrapped around at least a portion of at least one of the following locations on said animal: a toe, a foot, an ankle, a leg, a thigh, a hip, a torso, a shoulder, an arm, an elbow, a forearm, a wrist, a hand, a finger, a neck and a top portion of a head.

5. The method of claim 1, further comprising:
providing said light delivery module with an attachment mechanism that attaches said light delivery module to a selected region of skin of said animal; and
providing a portable power supply system, connected to and supplying power for said light delivery module.

6. The method of claim 5, further comprising providing said attachment mechanism as a bandaid having a shape that is substantially polygonal.

7. The method of claim 5, further comprising:
providing a second light delivery module and a second attachment mechanism that attaches said light delivery module to a second selected region of skin of said animal, where the second region is adjacent to said first region; and
connecting the second light delivery module to said power supply module so that delivery of electrical power to the second light delivery module is integrated with delivery of power to said first light delivery module.

8. The method of claim 7, further comprising providing each of said first attachment mechanism and said second attachment mechanism as a bandaid having a shape that is substantially polygonal, where said first and second attachment mechanisms can be positioned to be contiguous along a first selected boundary of said first attachment mechanism and a second selected boundary of said second attachment mechanism.

9. The method of claim 1, further comprising providing, as said light delivery module, a light delivery wrap, including at least one of said first and second light delivery elements, that is positioned adjacent to a lower portion of a head of said animal.

10. The method of claim 1, further comprising providing, as said light delivery module, a light delivery wrap, including at least one of said first and second light delivery elements, that is positioned adjacent to an upper portion of a head of said animal.

11. The method of claim 1, further comprising providing, as said light delivery module, a light delivery wrap, including at least one of said first and second light delivery elements, that comprises a first modular component positioned adjacent to a lower portion of a head of the animal and a second modular component positioned adjacent to an upper portion of the animal's head, wherein the first and second modular components together cover substantially all of the upper portion and the lower portion of said animal's head.

12. The method of claim 1, further comprising providing said light delivery module with a light delivery wrap covering substantially all of an upper portion and a lower portion of said animal's head and containing, on the light delivery wrap, at least one aperture for at least one of a group consisting of an eye, a nose, an ear and a mouth.

13. The method of claim 1, further comprising providing, as said light delivery module, a light delivery module that fits within said animal's mouth and illuminates a selected portion of an interior of said animal's mouth.

14. The method of claim 13, further comprising illuminating, with said light delivery module, at least one of a tooth, a gum region adjacent to the tooth, and a portion of a roof in said animal's mouth.

15. The method of claim 13, further comprising deflating or compressing said light delivery module before insertion into said animal's mouth and inflating or de-compressing said light delivery module after insertion of said light delivery module into said animal's mouth.

16. The method of claim 1, further comprising providing, as said light delivery module, a light delivery module that fits within a cavity of said animal used for reproduction and illuminates a selected portion of an interior of the cavity of said animal.

17. The method of claim 16, further comprising deflating or compressing said light delivery module before insertion into said cavity and inflating or de-compressing said light delivery module after insertion into said cavity.

18. The method of claim 1, further comprising providing, as said light delivery module, a light delivery module that attaches to a selected portion of skin of said animal and provides illumination that induces a medical healing process in a vicinity of the selected portion of the skin.

19. The method of claim 18, further comprising providing a portable power supply, carried by or attached to said animal, for said light delivery module.

20. The method of claim 18, further comprising choosing said selected portion of said skin adjacent to, or coincident with, an acupuncture meridian for said animal.

21. The method of claim 1, further comprising exposing said selected body component to substantially no light within said first and second selected wavelength ranges and to substantially no light within said third and fourth selected wavelength ranges, during said dark time interval.

22. The method of claim 1, further comprising choosing at least one of said first wavelength range, said second wavelength range, said third wavelength range and said fourth wavelength range to be contained in an overall wavelength range 350 nm $\leq \lambda \leq$ 1500 nm.

23. The method of claim 1, further comprising exposing said body component to said light having an energy delivery rate r lying in a range 0.0013 Joules/cm$^2$/sec$\leq$r$\leq$0.02 Joules/cm$^2$/sec, during at least one of said first time interval and said second time interval.

24. The method of claim 1, further comprising exposing said body component to said light having an accumulated energy density E(accum) lying in a range 2.5 Joules/cm$^2$$\leq$E (accum)$\leq$20 Joules/cm$^2$.

25. The method of claim 1, further comprising choosing a length $\Delta$t(exp) for at least one of said first time interval and said second time interval to lie in a range 0.1 sec$\leq$$\Delta$t(exp) $\leq$1 sec.

26. The method of claim 1, further comprising providing said body component with a low frequency (LF) electromagnetic field having at least one frequency f in a range 1 Hz$\leq$f$\leq$10$^4$ Hz.

27. The method of claim 26, further comprising including at least one of the following frequencies f in said low frequency field: 1.7 Hz, 4 Hz, 8 Hz, 80 Hz, 266 Hz and 666 Hz.

28. The method of claim 1, further comprising providing said body component with a magnetic field, oriented in a selected direction and having an intensity B in a range of about 100 Gauss$\leq$B$\leq$10$^4$ Gauss.

29. The method of claim 1, further comprising providing said body component with a low frequency magnetic field, oriented in a selected direction and having at least one frequency f in a range of about 1 Hz$\leq$f$\leq$10$^4$ Hz.

30. A system for illuminating an animal's body, the system comprising:
a light delivery module, having at least first and second light delivery elements for generating and focussing light to intermittently illuminate a selected component of a human's body with light having at least two wavelengths;
the first light delivery element being arranged to expose the body component to light in a first selected range of wavelengths for a first selected exposure time interval to produce at least one free electron within or adjacent to the body component;
the second light delivery element being arranged to expose the body component to light in a second selected range of wavelengths for a second selected exposure time interval to produce at least one free electron within or adjacent to the body component, where the first and second exposure time intervals are spaced apart by a dark time interval having a selected length $\Delta$t(dark) that is at least 0.1 sec,
where the at least one free electron produced during each of the first and second exposure time intervals is allowed to come to equilibrium within or adjacent to the body component.

31. The system of claim 30, wherein at least one of said first, second, third and fourth wavelength ranges includes at least one of the following wavelengths: 470 nm, 550 nm, 637 nm, 666 nm, 890 nm and 905 nm.

32. The system of claim 30, wherein said light delivery module is provided with a light delivery wrap that is configured to be wrapped around at least a portion of at least one of the following locations on said animal: a toe, a foot, an ankle, a leg, a thigh, a hip, a torso, a shoulder, an arm, an elbow, a forearm, a wrist, a hand, a finger, a neck and a top portion of a head.

33. The system of claim 32, wherein at least one of said first and second light delivery elements comprises:
an attachment mechanism that attaches said at least one light delivery element to a selected region of skin of said animal; and
a portable power supply system, connected to and supplying power for said at least one light delivery element.

34. The system of claim 33, wherein said attachment mechanism is provided as a bandaid having a shape that is substantially polygonal.

35. The system of claim 33, further comprising:
a second light delivery module and a second attachment mechanism that attaches said light delivery module to a second selected region of skin of said animal, where the second region is adjacent to said first region;
wherein the second light delivery module is connected to said power supply module so that delivery of electrical power to the second light delivery module is integrated with delivery of power to said first light delivery module.

36. The system of claim 35, wherein each of said first attachment mechanism and said second attachment mechanism is provided as a bandaid having a shape that is substantially polygonal, where said first and second attachment mechanisms can be positioned to be contiguous along a first selected boundary of said first attachment mechanism and a second selected boundary of said second attachment mechanism.

37. The system of claim 30, further comprising a light delivery wrap, including at least one of said first and second light delivery elements, that can be positioned adjacent to a lower portion of a head of said animal.

38. The system of claim 30, further comprising a light delivery wrap, including at least one of said first and second light delivery elements, that can be positioned adjacent to an upper portion of a head of said animal.

39. The system of claim 30, further comprising a light delivery module that fits within said animal's mouth and illuminates a selected portion of an interior of said animal's mouth.

40. The system of claim 39, wherein at least one of a tooth, a gum region adjacent to the tooth and a portion of a roof in said animal's mouth is illuminated with said light delivery module.

41. The system of claim 39, wherein said light delivery module can be deflated or compressed before insertion into said animal's mouth and said light delivery module can be inflated or de-compressed after insertion of said light delivery module into said animal's mouth.

42. The system of claim 30, further comprising a light delivery module that fits within a cavity of said animal used for reproduction and illuminates a selected portion of an interior of the cavity of said animal.

43. The system of claim 42, wherein said light delivery module can be deflated or compressed before insertion into said cavity and said light delivery module can be inflated or de-compressed after insertion into said cavity.

44. The system of claim 30, wherein said light delivery module attaches to a selected portion of skin of said animal and provides illumination that induces a medical healing process in a vicinity of the selected portion of the skin.

45. The system of claim 44, wherein said selected portion of said skin is chosen adjacent to, or coincident with, an acupuncture meridian for said animal.

46. The system of claim 30, wherein said selected body component is exposed to substantially no light within said first and second selected wavelength ranges and to substantially no light within said third and fourth selected wavelength ranges, during said dark time interval.

47. The system of claim 30, wherein at least one of said first wavelength range, said second wavelength range, said third wavelength range and said fourth wavelength range is contained in an overall wavelength range 350 nm$\leq\lambda\leq$1500 nm.

48. The system of claim 30, wherein a length $\Delta t(exp)$ for at least one of said first time interval and said second time interval lies in a range 0.1 sec$\leq\Delta t(exp)\leq$1 sec.

49. The system of claim 30, further comprising an electromagnetic field source that provides said body component with a low frequency (LF) electromagnetic field having at least one frequency f in a range 1 Hz$\leq f\leq 10^4$ Hz.

50. The system of claim 49, wherein said at least one frequency f includes at least one of the following frequencies f in said low frequency field: 1.7 Hz, 4 Hz, 8 Hz, 80 Hz, 266 Hz and 666 Hz.

51. The system of claim 30, further comprising a magnetic field source that provides said body component with a magnetic field, oriented in a selected direction and having an intensity B in a range of about 100 Gauss$\leq B\leq 10^4$ Gauss.

52. The system of claim 30, further comprising a magnetic field source that provides said body component with a low frequency magnetic field, oriented in a selected direction and having at least one frequency f in a range of about 1 Hz$\leq f\leq 10^4$ Hz.

* * * * *